United States Patent [19]

Matsuo et al.

[11] 4,282,372

[45] Aug. 4, 1981

[54] PROCESS FOR PRODUCING CYCLOPENTENOLONES

[75] Inventors: Takashi Matsuo, Itami; Kazunori Tsushima, Nishinomiya, both of Japan

[73] Assignee: Sumitomo Chemical Company, Limited, Osaka, Japan

[21] Appl. No.: 89,351

[22] Filed: Oct. 30, 1979

[30] Foreign Application Priority Data

Nov. 1, 1978 [JP] Japan .................. 53-135386
Nov. 1, 1978 [JP] Japan .................. 53-135387
Nov. 15, 1978 [JP] Japan .................. 53-141410
Nov. 15, 1978 [JP] Japan .................. 53-141411

[51] Int. Cl.$^3$ .................. C07C 45/57; C07C 67/00
[52] U.S. Cl. .................. 560/121; 562/503; 568/322; 568/361; 260/346.11; 260/347.8; 260/347.4; 260/347.5; 260/347.3; 260/347.91; 260/348.49; 260/348.57; 260/348.25
[58] Field of Search .................. 260/586 R, 590 C; 560/121; 562/503; 568/322, 361

[56] References Cited

PUBLICATIONS

Elming, Adv. in Org. Chem., vol. 2, pp. 67-75 (1960).
Floyd, J. Org. Chem., vol. 43, #9, pp. 1641-1643 (1978).
Shono et al., Chem. Lett., pp. 1249-1252 (1976).

*Primary Examiner*—Nicky Chan
*Assistant Examiner*—James H. Reamer
*Attorney, Agent, or Firm*—Stevens, Davis, Miller & Mosher

[57] ABSTRACT

A novel process for producing cyclopentenolones, useful intermediates for producing agricultural chemicals and prostaglandins of the formula (I), (I)

wherein $R_1$ is a hydrogen atom or a lower alkyl group, and $R_2$ is a hydrogen atom, a lower alkyl, lower alkenyl or lower alkynyl group or a group of the formula, in which $R_4$ is a hydrogen atom, a methyl group or a halogen atom), $-CH_2-CH=CH-(CH_2)_3-CO_2R_5$, or $-(CH_2)_5-CO_2R_5$ (in which $R_5$ is a hydrogen atom or a lower alkyl group), but $R_1$ and $R_2$ are not a hydrogen atom at the same time, characterized in that said cyclopentenolones are derived from a starting material of the formula (III), (III)

through intermediates of the formulae (IV), (V) and (II), (IV)   (V)

(II)

Many of the intermediates are novel compounds.

3 Claims, No Drawings

PROCESS FOR PRODUCING CYCLOPENTENOLONES

The present invention relates to a novel process for producing cyclopentenolones. More particularly, it provides a novel process for producing cyclopentenolones of the following formula (I) which are useful intermediates for producing agricultural chemicals and prostagrandins:

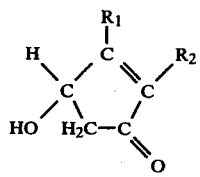

wherein $R_1$ is a hydrogen atom or a $C_1$–$C_6$ alkyl group, and $R_2$ is a hydrogen atom, a $C_1$–$C_8$ alkyl, $C_2$–$C_8$ alkenyl or $C_2$–$C_8$ alkynyl group or a group of the formula,

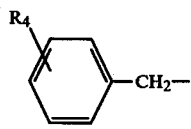

[in which $R_4$ is a hydrogen atom, a methyl group or a halogen atom (chlorine, bromine and fluorine)], —CH$_2$—CH=CH—(CH$_2$)$_3$—CO$_2$R$_5$, or —(CH$_2$)$_6$—CO$_2$R$_5$ (in which $R_5$ is a hydrogen atom or a $C_1$–$C_4$ alkyl group), but $R_1$ and $R_2$ are not a hydrogen atom at the same time.

Allethrin, well known as a useful agricultural chemical, was invented by M. S. Schechter in 1949, and because of its excellent insecticidal activity and low toxicity, it has found a wide application in the world, and also many studies to synthesize it have been made. In the studies, many proposals have also been made on the synthesis of the alcohol moiety of Allethrin, and some of them are now in practical use. But they are not always satisfactory in industry in terms of yield, troublesome operation and environmental problems.

For the reasons as described above, the inventors extensively studied how to produce cyclopentenolones used as intermediates for this insecticidal compound, and found a novel, very advantageous process. The inventors further examined this process thoroughly to complete the present invention.

That is, the present invention provides a novel process for producing cyclopentenolones of the foregoing formula (I) characterized by reacting a substituted furan derivative of the formula (II),

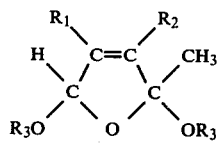

wherein $R_1$ and $R_2$ have the same meanings as above and $R_3$ is a $C_1$–$C_4$ alkyl group, under an acidic condition.

Also, in the present invention, the substituted furan derivatives of the formula (II) are novel compounds not disclosed in the literature and can be obtained from well-known compounds, for example, by the following method:

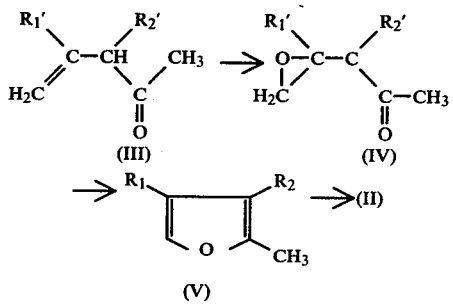

wherein $R_1$ and $R_2$ have the same meanings as above, and $R_1'$ is a hydrogen atom or a $C_1$–$C_6$ alkyl group, and $R_2'$ is a hydrogen atom, a $C_1$–$C_8$ alkyl, $C_2$–$C_8$ alkenyl or $C_2$–$C_8$ alkynyl group or a group of the formula,

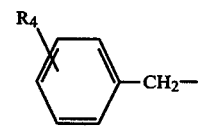

[in which $R_4$ is a hydrogen atom, a methyl group or a halogen atom (chlorine, bromine and fluorine)], but $R_1$ and $R_2$ are not both a hydrogen atom.

That is, the furan derivatives (II) can be obtained by oxidizing a well-known keto compound of the formula (III) to obtain an epoxy-ketone compound of the formula (IV), dehydrating the resulting compound (IV) with a base or acid to obtain a furan compound of the formula (V), and then reacting the resulting compound (V) with chlorine or bromine in an alcohol of the formula (VI), $$R_3\text{—OH} \qquad (VI)$$

wherein $R_3$ has the same meaning as above, in the presence of an alkali.

That is, according to the present invention, cyclopentenolones, important intermediates for producing agricultural chemicals or prostaglandins, can be produced very advantageously in industry in terms of the number of reaction steps, operation and yield.

Next, every stage of the process will be explained in detail.

Stage A

Process for producing the compound of the formula (I) from the compound of the formula (II)

Cyclopentenolones of the formula (I) are produced by reacting a substituted furan compound of the formula (II),

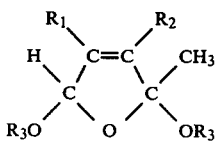

wherein $R_1$, $R_2$ and $R_3$ have the same meanings as above, under an acidic condition.

A reagent used for making the acidic reaction condition may be any of those which shows an acidity (i.e. below pH 7) in an aqueous solution. Specifically, the following acids are used.

1. Inorganic acids

There may be given as examples the so-called mineral acids such as hydrochloric acid, sulfuric acid, phosphoric acid, boric acid and the like.

2. Organic acids

Organic acids can be roughly divided into fatty acids and aromatic acids. Specifically, monobasic fatty acids include for example acetic acid and propionic acid, and polybasic ones include for example oxalic acid and tartaric acid. Monobasic aromatic acids include for example benzoic acid, p-chlorobenzoic acid and phenol, and polybasic ones include for example phthalic acid.

3. Salts of inorganic acid

There may be used for example alkali metal salts, alkaline earth metal salts or ammonium salts of inorganic acids. More particularly, the alkali metal salts include for example potassium dihydrogen phosphate, potassium monohydrogen phosphate, sodium monohydrogen phosphate and sodium dihydrogen phosphate. The alkaline earth metal salts include for example calcium chloride and the ammonium salts include for example ammonium chloride and ammonium sulfate.

4. Salts of organic acid

There may be used alkali metal salts or ammonium salts of organic acids. More particularly, the alkali metal salts include for example potassium phthalate, potassium hydrogen phthalate and sodium hydrogen tartarate, and the ammonium salts include for example ammonium hydrogen phthalate and ammonium hydrogen tartarate.

The reaction of the present invention is not restricted by solvents. As the solvent, however, there may be mentioned water, alcohols, ethers (e.g. tetrahydrofuran, dioxane), ketones (e.g. acetone, methyl ethyl ketone) or hydrocarbons (e.g. hexane, benzene, toluene). These solvents may be used in combination. The reaction temperature of the present invention is not particularly limited, and it is the commonly employed ones. Generally, however, it is preferably within a range of 0° C. to the boiling point of the solvent.

The reaction time of the present invention varies with the starting material, acid, solvent and reaction temperature, but generally it is within a range of 5 minutes to 50 hours.

In the present compounds of the formula (I), specific examples of $R_1$ include for example a hydrogen atom and alkyl groups (e.g. methyl, ethyl, propyl). Specific examples of $R_2$ include for example alkyl groups (e.g. methyl, ethyl, propyl), alkenyl groups (e.g. allyl, 2-butenyl), alkynyl groups (e.g. 2-propynyl, 2-butynyl) and benzyl, p-fluorobenzyl, p-bromobenzyl, p-chlorobenzyl, 6-carboethoxy-2-hexenyl and 6-carboethoxy-hexyl groups.

In the substituted furan derivatives of the formula (II), specific examples of $R_3$ include for example methyl, ethyl and propyl groups.

Stage B

Process for producing the compound of the formula (II) from the compound of the formula (V)

The novel furan compounds of the formula (II),

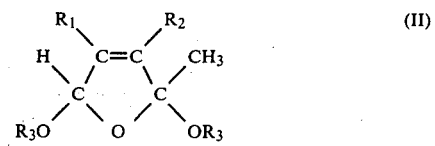

wherein $R_1$, $R_2$ and $R_3$ have the same meanings as above, are produced by reacting a compound of the formula (V),

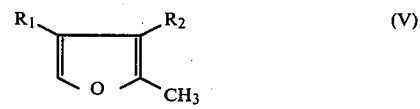

wherein $R_1$ and $R_2$ have the same meanings as above, with chlorine or bromine in an alcohol of the formula (VI),

wherein $R_3$ has the same meaning as above, in the presence of an alkali.

In carrying out the present invention, solvents other than the alcohol of the formula (VI),

wherein $R_3$ has the same meaning as above, are not particularly necessary, but if necessary the alcohol may be used as a mixture with benzene, toluene, hexane, tetrahydrofuran or water. The reaction temperature is not particularly limited, but it is within a range of $-70°$ C. to the boiling point of the solvent, preferably $-50°$ to 30° C.

It is necessary that the molar ratio of $R_3OH$ to the compound (V) is 2 or more. As the alkali used herein, alkali carbonates such as potassium carbonate and sodium carbonate are preferably used. A suitable amount of the alkali used in not smaller than 2 equivalents to not larger than 10 equivalents based on the compound (V). The molar ratio of chlorine or bromine to the compound (V) is commonly 1.0 to 1.2. The reaction time varies with the materials, alkali, chlorine or bromine, solvent and reaction temperature, but generally it is a moment to a maximum of 10 hours.

In the present compounds of the formula (II), specific examples of $R_1$ include for example a hydrogen atom and alkyl groups (e.g. methyl, ethyl, propyl). Those of $R_2$ include for example alkyl groups (e.g. methyl, ethyl, propyl), alkenyl groups (e.g. allyl, 2-butenyl), alkynyl groups (e.g. 2-propynyl, 2-butyn-1-yl), benzyl, p-fluorobenzyl, p-bromobenzyl and p-chlorobenzyl groups and groups of the formulae, $-CH_2-CH=CH-(CH_2)_3-CO_2R_5$ and $-(CH_2)_6-CO_2R_5$ (in which $R_5$ is a hydrogen atom or alkyl groups such as methyl, ethyl and propyl). Specific examples of $R_3$ include for example methyl, ethyl and propyl groups.

Of the furan compounds of the formula (II) produced by the stage B, those in which $R_1$ is a hydrogen atom or a $C_1-C_6$ alkyl group, $R_2$ is a $C_1-C_8$ alkyl, $C_2-C_8$ alkenyl or $C_2-C_8$ alkynyl group or a group of the formula,

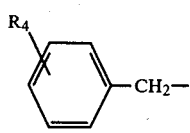

(in which $R_4$ is a hydrogen atom, a methyl group or a halogen atom such as chlorine, bromine or fluorine) and $R_3$ is a $C_1$–$C_4$ alkyl group, are novel compounds.

Stage C

Process for producing the compound of the formula (V') from the compound of the formula (IV)

The furan compounds of the formula (V'),

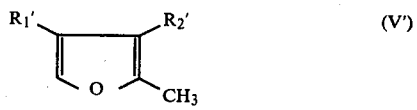

wherein $R_1'$ and $R_2'$ have the same meanings as above, are produced by subjecting an epoxyketone compound of the formula (IV),

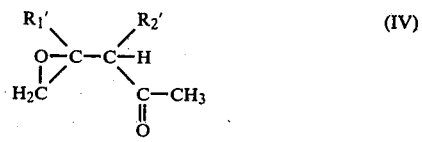

wherein $R_1'$ and $R_2'$ have the same meanings as above, to dehydration reaction in the presence of a base or acid.

In carrying out the present invention, the acid used includes for example mineral acids (e.g. hydrochloric acid, sulfuric acid), lower fatty acids (e.g. oxalic acid, formic acid, acetic acid, propionic acid), $BF_3$ etherate and phenols. The base includes for example potassium carbonate, sodium carbonate, potassium hydroxide, sodium hydroxide, sodium methylate, sodium ethylate, potassium tert-butoxide, alumina and glass powder.

The reaction time varies with the materials, base, acid, solvent and reaction temperature, but generally it is 30 minutes to a maximum of 72 hours.

The reaction temperature is not particularly limited, but generally it is within a range of $-20°$ to $250°$ C., preferably $0°$ to $200°$ C.

The reaction of the present invention proceeds in the presence of the base or acid. The amount of the base or acid is generally 0.01 mole or more, preferably 2 moles, based on the compound (IV).

In many cases, a solvent is not particularly necessary, but a solvent such as water, methanol, ethanol, benzene, toluene, xylene, hexane, tetrahydrofuran, dimethylformamide, dimethyl sulfoxide or the like may be used if necessary.

In the present compounds of the formula (V), specific examples of $R_2$ include for example allyl, 2-butenyl, 2-propynyl, 2-butyn-1-yl, benzyl, p-chlorobenzyl, p-bromobenzyl, p-fluorobenzyl and p-methylbenzyl groups.

The furan compound of the formula (V), wherein $R_1$ is a hydrogen atom and $R_2$ is a group of the formulae, —$CH_2$—$CH$=$CH$—$(CH_2)_3$—$CO_2R_5$ and —$(CH_2)_6$—$CO_2R_5$ (in which $R_5$ is a hydrogen atom or $C_1$–$C_4$ alkyl groups) are produced by following method.

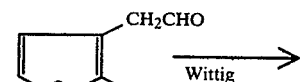

2-methyl-3-furan-acetaldehyde*

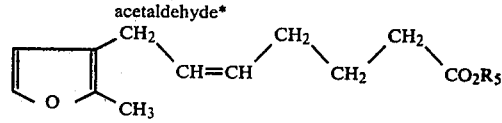

NMR data ($CDCl_3$, δ values on TMs standard)
1.15 (t, 3H)
2.18 (s, 3H)
3.10 (d, 2H)
4.10 (q, 2H)
5.30 (m, 2H)
6.18 (d, J = 2 Hz, 1H)
7.15 (d, J = 2 Hz, 1H)

Pd/C/H₂ or PtO₂/H₂ catalytic reduction (ca. 20° C. 3 hrs. Solvent ACOEt)

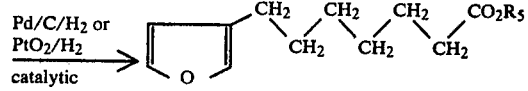

NMR data ($CCl_4$, δ value on TMS standard
2.10 (s, 3H)
2.3 (m, 2H)
2.6 (m, 2H)
4.10 (q, 2H)
6.05 (d, J = 2 Hz, 1H)
7.05 (d, J = 2 Hz, 1H)

*Helv. Chin. Acta 53 605 (1970)
**J. Org. Chem. 43 1641 (1978)

Of the furan compounds of the formula (V) produced by the stage C, those in which $R_1$ is a methyl group, $R_2$ is a $C_2$–$C_8$ alkenyl or $C_2$–$C_8$ alkynyl group or a group of the formula,

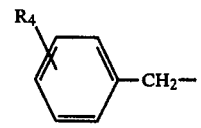

[in which $R_4$ is a hydrogen atom, a methyl group or a halogen atom (chlorine, bromine or fluorine)], and $R_1$ is a hydrogen atom, $R_2$ is groups of the formulae, —$CH_2$—$CH$=$CH$—$(CH_2)_3$—$CO_2R_5$ and —$(CH_2)_6$—$CO_2R_5$ (in which $R_5$ is a hydrogen atom or $C_1$–$C_4$ alkyl group) are novel compounds.

Stage D

Process for producing the compound of the formula (IV) from the compound of the formula (III)

The novel epoxyketone compounds of the formula (IV),

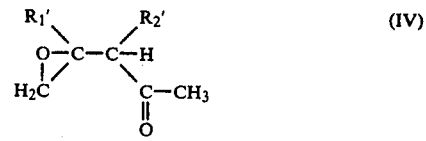

wherein $R_1'$ and $R_2'$ have the same meanings as above, are produced by oxidizing a ketone compound of the formula (III),

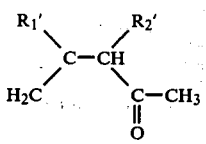

wherein $R_1'$ and $R_2'$ have the same meanings as above.

As the oxidizing agent used in the present invention, there may be mentioned m-chloroperbenzoic acid, perbenzoic acid, peracetic acid, p-nitroperbenzoic acid, monoperoxyphthalic acid, trifluoroperacetic acid and the like. But, the oxidizing agent is not limited to these examples.

The reaction of the present invention is not restricted by solvents, but it may be carried out in a solvent such as water, tetrahydrofuran, diethyl ether, chloroform, dichloromethane, acetic acid, benzene, toluene or the like. These solvents may be used in combination. The reaction temperature of the present invention is not particularly limited, and it is the commonly employed ones. Generally, however, it is preferably within a range of $-40°$ to $30°$ C.

The reaction time varies with the starting materials, oxidizing agent, solvent and reaction temperature, but generally it is within a range of 10 minutes to 48 hours.

It is suitable that the molar ratio of the oxidizing agent to the compound (III) is not smaller than 1 to not larger than 10.

In the present compounds of the formula (IV), specific examples of $R_1'$ include a hydrogen atom and a methyl group. Those of $R_2'$ include for example alkyl groups (e.g. methyl, ethyl, propyl), alkenyl groups (e.g. allyl, 2-butenyl), alkynyl groups (e.g. 2-propynyl, 2-butyn-1-yl), benzyl, p-fluorobenzyl, p-bromobenzyl and p-chlorobenzyl groups.

Of the epoxyketone compounds of the formula (IV) produced by the stage D, those in which $R_1'$ is a hydrogen atom or a $C_1$-$C_6$ alkyl group and $R_2'$ is a $C_1$-$C_8$ alkyl, $C_2$-$C_8$ alkenyl or $C_2$-$C_8$ alkynyl group or a group of the formula,

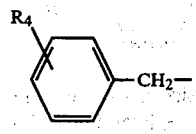

(in which $R_4$ is a hydrogen atom, a methyl group or a halogen atom such as chlorine, bromine and fluorine), are novel compounds.

The ketone compound of the formula (III) may be synthesized, for instance, by the methods as disclosed in Agr. Biol. Chem. 28 95–104 (1964) and C.R. Acad. Sc., Paris, Serie C, 1614–1616 (1968).

Next, the present invention will be illustrated in more detail with reference to the following examples, but the present invention is not of course limited to these examples.

STAGE A

EXAMPLE 1

Three hundred milligrams of a furan compound of the formula (II) ($R_1=CH_3$, $R_2=$—$CH_2$—$CH=CH_2$, $R_3=CH_3$) was added to a dioxane/water mixture (dioxane 3.0 ml, water 2.0 ml), and then hydroquinone (10 mg) was added thereto. To the solution was added a phosphate buffer solution [a solution of potassium dihydrogen phosphate (0.27 g) and sodium monohydrogen phosphate (0.36 g) in water (5.0 ml)], followed by refluxing for 90 minutes. After adding water (10 ml) to the reaction solution, the solution was saturated with sodium chloride and extracted twice with ether. The ether layer was dried over magnesium sulfate, and the solvent was removed by evaporation. By column chromatography on silica gel, 135 mg of allethrolone (2-methyl-3-allyl-cyclopent-2-en-4-on-1-ol) was obtained.

Yield: 58%.

NMR (CDCl$_3$, $\delta$ values on TMS standard): 2.15 (s, 3H), 2.35 (d), 2.60 (d), 2H, 2.90 (d, 2H), 3.1 (BS, 1H, —OH), 4.5–6.0 (m, 4H).

EXAMPLE 2

830 Milligrams of a furan compound of the formula (II) ($R_1=H$, $R_2=$

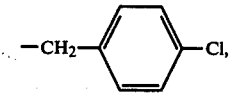

$R_3=CH_3$) was added to a mixture of dioxane (30 ml) and water (20 ml), and 10% hydrochloric acid (4 ml) was then added thereto, followed by refluxing for 9 hours. Water (100 ml) was added to the reaction solution which was then saturated with sodium chloride and extracted three times with ethyl acetate. The ethyl acetate layer was washed with an aqueous sodium hydrogen carbonate solution and then with an aqueous sodium chloride solution. The solvent was removed by evaporation, and the residue was column chromatographed on silica gel to obtain 140 mg of 3-p-chlorobenzylcyclopent-2-en-4-on-1-ol as a pale yellow oil.

Yield: 20%.

Refractive index: 1.5741 (22° C.).

NMR data (CDCl$_3$, $\delta$ values on TMS standard): 2.16 (q, 1H), 2.74 (q, 1H), 3.39 (m, 2H), 4.71 (m, 1H), 6.93 (m, 1H), 7.11 (m, 4H).

EXAMPLE 3

1.0 Gram of a furan compound of the formula (II) ($R_1=CH_3$, $R_2=$—$CH_2$—$C\equiv CH$, $R_3=CH_3$), toluene (10 ml), water (25 ml), potassium dihydrogen phosphate (0.58 g) and sodium monohydrogen phosphate (0.11 g) were mixed and vigorously stirred at 45° C. for 50 hours. The aqueous layer of the reaction solution was saturated with sodium chloride, and the solution was separated into two layers. The aqueous layer was extracted three times with ethyl acetate. The toluene layer and ethyl acetate layer were combined, and the solvent was removed by evaporation. The residual oil was column chromatographed on silica gel to obtain 260 mg of the objective 2-methyl-3-(2'-propynyl)-cyclopent-2-en-4-on-1-ol as a pale yellow oil.

Yield: 34%.

Refractive index (19.5° C.): 1.5345.

NMR data (CDCl$_3$, $\delta$ values on TMS standard): 1.95 (t, 1H), 2.18 (s, 3H), 2.3–2.9 (m, 2H), 3.05 (d, 2H), 4.68 (1H).

EXAMPLE 4

440 Milligrams of a furan compound of the formula (II) ($R_1=H$, $R_2=$

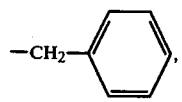

$R_3=CH_3$) and hydroquinone (10 mg) were added to a mixture of dioxan (10 ml) and water (15 ml), and then potassium dihydrogen phosphate (0.72 g) and sodium monohydrogen phosphate (0.96 g) were added thereto, followed by refluxing for 90 minutes. The reaction solution was after-treated in the same manner as in Example 4 and column chromatographed on silica gel to obtain 210 mg of the objective 3-benzylcyclopent-2-en-4-on-1-ol.

Yield: 59.4%.

Refractive index (20.5° C.): 1.5662.

NMR data (CDCl$_3$, δ values on TMS standard): 2.16 (q, 1H), 2.72 (q, 1H), 3.40 (m, 2H), 4.75 (m, 1H), 6.85 (m, 1H), 7.08 (m, 5H).

EXAMPLE 5

2.09 Grams of a furan compound of the formula (II) ($R_1=H$, $R_2=$

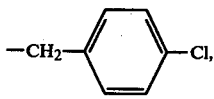

$R_3=CH_3$) was dissolved in a mixture of dioxane (20 ml) and water (20 ml), and then potassium dihydrogen phosphate (0.72 g) and sodium monohydrogen phosphate (0.96 g) were added thereto, followed by refluxing for 13 hours. The reaction solution was after-treated in the same manner as in Example 4 and column chromatographed on silica gel to obtain 0.89 g of the unreacted material and 0.88 g of the objective 3-p-chlorobenzyl-cyclopent-2-en-4-on-1-ol. The yield is 89% considering the recovery of the material.

Refractive index (22° C.): 1.5741.

EXAMPLE 6

370 Milligrams of a furan compound of the formula (II) ($R_1=CH_3$, $R_2=-CH_2-CH=CH_2$, $R_3=CH_3$), potassium dihydrogen phosphate (0.27 g), sodium monohydrogen phosphate (0.36 g) and water (5 ml) were mixed and stirred at 25° C. for 12 hours. The reaction solution was aftertreated in the same manner as in Example 4 and column chromatographed on silica gel to obtain 82 mg of allethrolone as a pale yellow oil.

Yield: 29%.

EXAMPLE 7

To 2,4-dimethyl-2,5-dimethoxy-2,5-dihydrofuran (1.6 g) were added 10 ml of a buffer solution (pH 6; prepared from potassium dihydrogen phosphate and sodium monohydrogen phosphate) and tetrahydrofuran (4 ml), and the mixture was refluxed for 5 hours. The reaction solution was extracted with ether to remove the unreacted materials, and the aqueous layer was concentrated. Ethyl acetate was added to the concentrate, followed by thorough stirring and filtering. The ethyl acetate layer was concentrated, and the residue was distilled to obtain 0.58 g of 2-methyl-cyclopent-2-en-4-on-1-ol.

Yield: 52%.

Boiling point: 85°–95° C./0.3 mmHg.

EXAMPLE 8

2,4-Dimethyl-3-ethyl-2,5-dimethoxy-2,5-dihydrofuran (9.3 g) was added to a mixture of 100 ml of a buffer solution (pH 5; prepared from potassium hydrogen phthalate and sodium hydrogen carbonate) and tetrahydrofuran (50 ml), and the mixture was refluxed for 1 hour. The reaction solution was poured into water, saturated with sodium chloride and extracted three times with ethyl acetate. The ethyl acetate layer was concentrated, and the residue was distilled to obtain 4.3 g of 2-methyl-3-ethyl-cyclopent-2-en-4-on-1-ol.

Yield: 62%.

Boiling point: 100°–110° C./0.5 mmHg.

EXAMPLE 9

600 Milligrams of 2-methyl-3-(6'-ethoxycarbonylhex-2'-en-1'-yl)-2,5-dimethoxy-2,5-dihydrofuran was added to a mixture of 5 ml of a buffer solution (pH 6; prepared in the same manner as in Example 7) and dioxane (3 ml), and the mixture was refluxed for 10 hours. The reaction solution was poured into water and extracted three times with ethyl acetate. After removing the solvent by evaporation, the residue was column chromatographed on silica gel to obtain 262 mg of 3-(6'-ethoxycarbonyl-hex-2'-en-1'-yl)-cyclopent-2-en-4-on-1-ol.

Yield: 52%.

NMR data (CDCl$_3$, δ values on TMS standard): 1–3 (13H, complex), 4.13 (2H, q), 4.90 (1H, m), 5.40 (2H, m), 7.14 (1H, m).

EXAMPLE 10

150 Milligrams of 2-methyl-3-(6'-ethoxycarbonyl-1'-hexyl)-2,5-dimethoxy-2,5-dihydrofuran was added to a mixture of 3 ml of a buffer solution (pH 6; prepared in the same manner as in Example 1) and tetrahydrofuran (2 ml), and the mixture was refluxed for 5 hours. The reaction solution was poured into water and extracted three times with ethyl acetate. After removing the solvent by evaporation, the residue was column chromatographed on silica gel to obtain 74 mg of 3-(6'-ethoxycarbonyl-1'-hexyl)-cyclopent-2-en-4-on-1-ol.

Yield: 58%.

NMR data (CDCl$_3$, δ values on TMS standard): 1–3 (17H, complex), 4.15 (2H, q), 5.03 (1H, m), 7.20 (1H, m).

STAGE B

EXAMPLE 1

To a solution of 2,4-dimethyl-3-allylfuran (1.36 g) in methanol (20 ml) was added potassium carbonate (2.76 g) at −20° C. To this methanol solution was added dropwise a bromine/methanol mixture (bromine 1.60 g, methanol 10 ml) over 1 hour. The reaction mixture was stirred at −20° C. for 1 hour and then at room temperature for 30 minutes. After filtering the reaction solution, methanol was removed by evaporation. The residual liquor was extracted with addition of an aqueous sodium chloride solution and ether. The ether layer was washed with an aqueous sodium chloride solution and dried over magnesium sulfate. Ether was removed by evaporation to obtain 1.73 g of a colorless transparent oil. It was found by NMR analysis that this oil was a pure compound of the formula (II) ($R_1=CH_3$, $R_2=-CH_2-CH=CH_2$, $R_3=CH_3$).

Refractive index (22° C.): 1.4610.

Yield: 87%.

NMR data (CCl₄, δ values on TMS standard): 1.25 (s), 1.30 (s) 3H, 1.60 (s, 3H), 2.65 (d, 2H), 2.80 (s), 2.83 (s), 3.18 (s), 3.27 (s) 6H, 4.5–6.0 (4H).

EXAMPLE 2

To a solution of 2,4-dimethylfuran (0.96 g) in methanol (20 ml) was added potassium carbonate (2.76 g) at −20° C. To this methanol solution was added dropwise a bromine/methanol mixture (bromine 1.60 g, methanol 10 ml) over 1 hour.

The reaction mixture was stirred at −20° C. for 1 hour and then at room temperature for 30 minutes. After filtering the reaction solution, methanol was removed by evaporation. The residual liquor was extracted with addition of an aqueous sodium chloride solution and ether. The ether layer was washed with an aqueous sodium chloride solution and dried over magnesium sulfate. Ether was removed by evaporation to obtain 1.54 g of a colorless transparent oil. It was found by NMR analysis that this oil was pure 2,4-dimethyl-2,5-dimethoxy-2,5-dihydrofuran.

Yield: 98%.

Refractive index: 1.4501 (23° C.).

EXAMPLE 3

To a solution of 2,4-dimethyl-3-ethylfuran (1.24 g) in methanol (20 ml) was added potassium carbonate (2.76 g) at −20° C. To this methanol solution was added dropwise a bromine/methanol mixture (bromine 1.60 g, methanol 10 ml) over 1 hour.

The reaction mixture was stirred at −20° C. for 1 hour and then at room temperature for 30 minutes. After filtering the reaction solution, methanol was removed by evaporation. The residual liquor was extracted with addition of an aqueous sodium chloride solution and ether. The ether layer was washed with an aqueous sodium chloride solution and dried over magnesium sulfate. Ether was removed by evaporation to obtain 1.82 g of a colorless transparent oil. It was found by NMR analysis that this oil was pure 2,4-dimethyl-2,5-dimethoxy-3-ethyl-2,5-dihydrofuran.

Yield: 98%.

Refractive index: 1.4513 (24° C.).

EXAMPLE 4

To a solution of 2,4-dimethyl-3-2'-propynylfuran (1.34 g) in methanol (20 ml) was added potassium carbonate (2.76 g) at −20° C. To this methanol solution was added dropwise a bromine/methanol mixture (bromine 1.60 g, methanol 10 ml) over 1 hour.

The reaction mixture was stirred at −20° C. for 1 hour and then at room temperature for 3 minutes. After filtering the reaction solution, methanol was removed by evaporation. The residual liquor was extracted with addition of an aqueous sodium chloride solution and ether. The ether layer was washed with an aqueous sodium chloride solution and dried over magnesium sulfate. Ether was removed by evaporation to obtain 1.88 g of a colorless transparent oil. It was found by NMR analysis that this oil was pure 2,4-dimethyl-2,5-dimethoxy-3-2'-propynyl-2,5-dihydrofuran.

Yield: 96%.

Refractive index: 1.4670 (22° C.).

EXAMPLE 5

To a solution of 2-methyl-3-(3'-methylbenzyl)furan (1.86 g) in methanol (20 ml) was added potassium carbonate (2.76 g) at −20° C. To this methanol solution was added dropwise a bromine/methanol mixture (bromine 1.60 g, methanol 10 ml) over 1 hour.

The reaction mixture was stirred at −20° C. for 1 hour and then at room temperature for 30 minutes. After filtering the reaction solution, methanol was removed by evaporation. The residual liquor was extracted with addition of an aqueous sodium chloride solution and ether. The ether layer was washed with an aqueous sodium chloride solution and dried over magnesium sulfate. Ether was removed by evaporation to obtain 2.36 g of a colorless transparent oil. It was found by NMR analysis that this oil was pure 2-methyl-2,5-dimethoxy-3-(3'-methylbenzyl)-2,5-dihydrofuran.

Yield: 95%.

Refractive index: 1.5124 (23° C.).

EXAMPLE 6

To a solution of 2-methyl-3-(2'-fluorobenzyl)furan (1.9 g) in methanol (20 ml) was added sodium carbonate (2.76 g) at −20° C. To this methanol solution was added dropwise a bromine/methanol mixture (bromine 1.60 g, methanol 10 ml) over 1 hour.

The reaction mixture was stirred at −20° C. for 1 hour and then at room temperature for 30 minutes. After filtering the reaction solution, methanol was removed by evaporation. The residual liquor was extracted with addition of an aqueous sodium chloride solution and ether. The ether layer was washed with an aqueous sodium chloride solution and dried over magnesium sulfate. Ether was removed by evaporation to obtain 2.42 g of a colorless transparent oil. It was found by NMR analysis that this oil was pure 2-methyl-2,5-dimethoxy-3-(2'-fluorobenzyl)-2,5-dihydrofuran.

Yield: 96%.

Refractive index: 1.4998 (22° C.).

In a similar way to Example 4, the following two compounds are obtained.

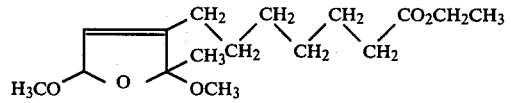

NMR data (CDCl₃, δ values on TMS standard)
1–2.7 (18H, complex), 3.03 (s), 3.10 (s) } 3H, 3.36 (s), 3.43 (s) } 3H, 4.15 (2H, q), 5.3–5.6 (2H, m).

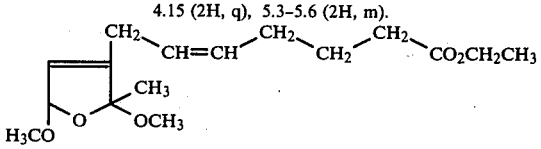

NMR data (CDCl₃, δ values on TMS standard)
1–2.9 (14H, complex)

3.03 (s), 3.09 (s) } 3H, 3.35 (s), 3.45 (s) } 3H, 4.15 (2H, q), 5.3–5.8 (4H, m)

STAGE C

EXAMPLE 1

A mixture of 3-allyl-4-methyl-4,5-epoxypentan-2-one (4.5 g) and glass powder (0.90 g) was stirred at a bath temperature of 220° C. for 10 hours in a nitrogen gas stream. After reaction, ether was added to the reaction mass, followed by drying over anhydrous magnesium sulfate. After removing the solvent by evaporation, the residue was distilled under reduced pressure to obtain 3.2 g of 2,4-dimethyl-3-allylfuran as a pale yellow oil.

Yield: 80.5%.

Boiling point: 130°–140° C./140 mmHg.

NMR data (CCl₄, δ values on TMS standard): 1.83 (d, 3H), 2.12 (s, 3H), 2.95 (dm, 2H), 4.5–5.0 (m, 3H), 6.82 (m, 1H).

EXAMPLE 2

3-Allyl-4-methyl-4,5-epoxy-pentan-2-one (4.50 g) was added to a 1% aqueous sodium carbonate solution (150 ml), followed by stirring for 2 hours at a bath temperature of 60° to 65° C. The reaction solution was extracted three times with methylene chloride, and the methylene chloride layer was washed with an aqueous sodium chloride solution. After removing the solvent by evaporation, the residue was column chromatographed on silica gel (50 g) and developed with methylene chloride. From the first eluate (400 ml) was obtained 1.80 g of a pure objective 2,4-dimethyl-3-allylfuran.

Boiling point: 130°–140° C./140 mmHg.

NMR data (CCl₄, δ values on TMS standard): 1.83 (d, 3H), 2.12 (s, 3H), 2.95 (dm, 2H), 4.5–5.0 (m, 3H), 6.82 (m, 1H).

EXAMPLE 3

18.0 Grams of 3-(2'-propynyl)-4-methyl-4,5-epoxy-pentan-2-one was added to a solution of sodium hydroxide (0.5 g) in water (300 ml), and then thiophenol (0.4 g) was added thereto, followed by stirring at 30° C. for 50 hours. The reaction solution was extracted twice with ether. The ether layer was concentrated, and the residue was distilled to obtain 9.6 g of 2,4-dimethyl-3-2'-propynylfuran.

Boiling point: 70°–75° C./20 mmHg.

Yield: 60.5%.

Refractive index: 1.4337 (25° C.).

EXAMPLE 4

15.6 Grams of 3-butyl-4,5-epoxy-pentan-2-one was added to chloroform (300 ml), and then conc. hydrochloric acid (3 ml) was added thereto, followed by refluxing for 10 hours. The chloroform layer was washed with water and then with an aqueous sodium hydrogen carbonate solution, followed by concentrating. The residue was column chromatographed on silica gel to obtain 4.8 g of 2-methyl-3-butylfuran.

Yield: 35%.

Refractive index: 1.4081 (28° C.).

STAGE D

EXAMPLE 1

To a solution of 3-(2'-propynyl)-4-methylpent-4-en-2-one (3.3 g) in methylene chloride (20 ml) was added dropwise a solution of m-chloroperbenzoic acid (6.3 g) in methylene chloride (80 ml) at 0° C. The reaction mixture was stirred at 0° to 5° C. for 2 hours, and then at 20° C. for 12 hours. The reaction solution was washed twice with an aqueous sodium hydrogen carbonate solution and dried over anhydrous magnesium sulfate. The solvent was removed by evaporation to obtain 3.6 g of pure 3-(2'-propynyl)-4-methyl-4,5-epoxy-pentan-2-one as a colorless transparent oil.

Yield: 98%.

Boiling point: 95°–100° C./18 mmHg.

NMR data (CCl₄, δ values on TMS standard): 1.15 (s), 1.31 (s) 3H, 1.87 (t, 1H), 2.17 (s), 2.22 (s) 3H, 2.37–2.85 (m, 5H).

EXAMPLE 2

To a solution of 3-allyl-4-methyl-pent-4-en-2-one (20.0 g) in methylene chloride (100 ml) was added dropwise a solution of m-chloroperbenzoic acid (29 g) in methylene chloride (300 ml) at 0° to 5° C. The reaction mixture was stirred at 0° to 5° C. for 3 hours and then at 20° C. overnight. The reaction solution was progressively washed with an aqueous sodium hydrogen carbonate solution, aqueous sodium sulfite solution, aqueous sodium hydrogen carbonate solution and then with an aqueous sodium chloride solution. After removing the solvent by evaporation, the residue was distilled to obtain 7.2 g of the unreacted material and 5.2 g of the objective 3-allyl-4-methyl-4,5-epoxy-pentan-2-one.

Boiling point: 84°–85° C./22 mmHg.

NMR data (CDCl₃, δ values on TMS standard): 1.20 (s), 1.31 (s) 3H, 2.16 (s), 2.24 (s) 3H, 2.64 (s, 2H), 2–3 (3H), 5–6 (3H).

EXAMPLE 3

4.6 Grams of sodium acetate was dissolved at 20° C. in a mixture of 3-(2'-propynyl)-4-methyl-pent-4-en-2-one (22.7 g) and dichloromethane (200 ml), and then a 9% peracetic acid solution (282 g) was added dropwise thereto over 30 minutes. After stirring at 20° C. for 48 hours, the reaction solution was phase-separated with addition of water and dichloromethane. The aqueous layer was further extracted twice with dichloromethane. The combined dichloromethane layer was concentrated, and the residue was distilled to obtain 19.2 g of pure 3-(2'-propynyl)-4-methyl-4,5-epoxy-pentan-2-one.

Boiling point: 85°–95° C./10 mmHg.

Yield: 77%.

Refractive index: 1.4612 (18.5° C.).

EXAMPLE 4

2.5 Grams of sodium acetate was added at 30° C. to a mixture of 3-allyl-4-methyl-pent-4-en-2-one (5.0 g) and dichloromethane (100 ml), and then a 9% peracetic acid solution (153 g) was added dropwise thereto over 1 hour. After stirring at 30° C. for 4 hours, the reaction solution was treated in the same manner as in Example 3 to obtain 1.20 g of pure 3-allyl-4-methyl-4,5-epoxy-pentan-2-one.

Boiling point: 70°–73° C./12 mmHg.

EXAMPLE 5

To a solution of 3-butyl-4-penten-2-one (14.0 g) in dichloromethane (100 ml) was added m-chloroperbenzoic acid (26.0 g) at 0° to 5° C., and the mixture was stirred at the same temperature for 1 hour and then at 20° C. for 12 hours. The reaction solution was then poured into water, followed by phase separation. The dichloromethane layer was washed with an aqueous sodium hydrogen carbonate solution and then with an aqueous sodium sulfite solution, followed by concentrating. The residue was distilled to obtain 13.3 g of 3-butyl-4,5-epoxy-pentan-2-one.

Boiling point: 75°–85° C./15 mmHg.

Refractive index: 1.4312 (15° C.).

Yield: 85%.

What is claimed is:

1. A process for producing a cyclopentenolone derivative of the formula (I),

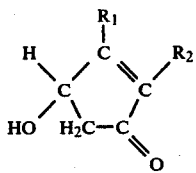 (I)

wherein $R_1$ is a hydrogen atom or a $C_1$-$C_6$ alkyl group, $R_2$ is a hydrogen atom, a $C_1$-$C_8$ alkyl group, a $C_2$-$C_8$ alkenyl group, a $C_2$-$C_8$ alkynyl group, a group of the formula,

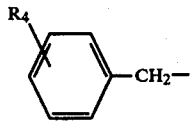

in which $R_4$ is a hydrogen atom, a methyl group or a halogen atom, or a group of the formula, —CH=CH—(CH$_2$)$_3$—CO$_2$R$_5$ or —(CH$_2$)$_6$—CO$_2$R$_5$ in which $R_5$ is a hydrogen atom or a $C_1$-$C_4$ alkyl group, and $R_1$ and $R_2$ are not a hydrogen atom at the same time, which comprises reacting a novel substituted furan derivative of the formula (II),

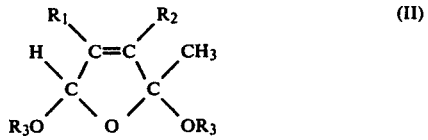 (II)

wherein $R_1$ and $R_2$ are as defined above, and $R_3$ is a $C_1$-$C_4$ alkyl group, in a solvent under acidic conditions.

2. The process according to claim 1, wherein the reaction is carried out in an aqueous solution of less than 7 in pH.

3. The process according to claim 1, wherein the reaction is carried out at a temperature of 0° C. to the boiling point of the solvent.

* * * * *